United States Patent
Wilson et al.

(10) Patent No.: US 8,447,075 B2
(45) Date of Patent: May 21, 2013

(54) SYSTEMS, METHODS AND DEVICES FOR USING ULTRASONIC PROBE PRESSURE INFORMATION IN ASSESSING MUSCLE TISSUE QUALITY

(75) Inventors: Doyle E. Wilson, Huxley, IA (US); Viren R. Amin, Ames, IA (US)

(73) Assignee: Biotronics, Inc., Ames, IA (US)

( * ) Notice: Subject to any disclaimer, the term of this patent is extended or adjusted under 35 U.S.C. 154(b) by 813 days.

(21) Appl. No.: 12/435,699

(22) Filed: May 5, 2009

(65) Prior Publication Data

US 2009/0274357 A1  Nov. 5, 2009

Related U.S. Application Data

(60) Provisional application No. 61/050,539, filed on May 5, 2008.

(51) Int. Cl.
*G06K 9/00* (2006.01)
(52) U.S. Cl.
USPC .......................................................... 382/110
(58) Field of Classification Search
USPC ... 382/128, 110; 600/407, 447, 547; 128/920; 73/602, 609, 618
See application file for complete search history.

(56) References Cited

U.S. PATENT DOCUMENTS

| 5,079,951 | A | | 1/1992 | Raymond et al. |
|---|---|---|---|---|
| 5,194,036 | A | | 3/1993 | Chevalier et al. |
| 5,208,747 | A | * | 5/1993 | Wilson et al. ................. 600/443 |
| 5,303,708 | A | * | 4/1994 | Stouffer ........................ 600/437 |
| 5,316,003 | A | * | 5/1994 | Stouffer ........................ 600/459 |
| 5,339,815 | A | | 8/1994 | Liu et al. |
| 5,353,796 | A | | 10/1994 | Schroeder et al. |
| 5,452,722 | A | | 9/1995 | Langton |
| 5,520,183 | A | | 5/1996 | Lake et al. |
| 5,613,493 | A | | 3/1997 | Schafer |
| 5,617,864 | A | | 4/1997 | Stouffer et al. |
| 5,625,147 | A | | 4/1997 | Miles et al. |
| 5,673,647 | A | | 10/1997 | Pratt |
| 5,685,307 | A | | 11/1997 | Holland et al. |
| 5,872,314 | A | | 2/1999 | Clinton |

(Continued)

FOREIGN PATENT DOCUMENTS

EP  1026516 B1  4/2006

OTHER PUBLICATIONS

R.K. Johnson, E.P. Berg, R. Goodwin, J.W. Mabry, R.K. Miller, O.W. Robinson, H. Sellers, and M.D. Tokach. Evaluation of procedures to predict fat-free lean in swine carcasses. J. of Anim. Sci. 2004. 82:2428-2441.

(Continued)

*Primary Examiner* — Joseph Chang
*Assistant Examiner* — Jeffrey Shin
(74) *Attorney, Agent, or Firm* — Crawford Maunu PLLC (57) ABSTRACT

Methods, systems and devices are implemented in connection with measuring characteristics of a portion of muscle tissue. Consistent with one such method an ultrasound probe is presented to the portion of muscle tissue. The probe produces a response-provoking signal in the muscle tissue, and the pressure applied between the probe and the portion of muscle tissue is sensed. A resulting signal is used to determine the muscle tissue characteristics based on the pressure being exerted between the probe and the portion. For example, the pressure data is associated with and used to filter the acquisition or use of ultrasound image data.

2 Claims, 6 Drawing Sheets

U.S. PATENT DOCUMENTS

| | | | |
|---|---|---|---|
| 5,944,598 | A | 8/1999 | Tong et al. |
| 5,960,105 | A | 9/1999 | Brethour |
| 6,084,407 | A | 7/2000 | Ellis |
| 6,099,473 | A | 8/2000 | Liu et al. |
| 6,104,827 | A | 8/2000 | Benn et al. |
| 6,167,759 | B1 | 1/2001 | Bond et al. |
| 6,170,335 | B1 | 1/2001 | Clinton |
| 6,198,834 | B1 | 3/2001 | Belk et al. |
| 6,200,210 | B1 | 3/2001 | Pratt |
| 6,322,508 | B1 | 11/2001 | Goldenberg et al. |
| 6,585,652 | B2 * | 7/2003 | Lang et al. ............ 600/449 |
| 6,591,681 | B1 * | 7/2003 | Shimada et al. ............ 73/600 |
| 6,730,034 | B1 * | 5/2004 | Lang et al. ............ 600/449 |
| 7,203,911 | B2 | 4/2007 | Williams |
| 7,860,547 | B2 * | 12/2010 | Kondoh et al. ............ 600/407 |
| 2007/0043290 | A1 * | 2/2007 | Goepp et al. ............ 600/437 |

OTHER PUBLICATIONS

Y. Liu and J.R. Stouffer. Pork carcass evaluation with an automated and computerized ultrasonic system. J. of Anim. Sci. 1995. 73:29-38.

D. Black, J. Vora, M. Hayward, and R. Marks. Measurement of subcutaneous fat thickness with high frequency pulse ultrasound: comparisons with a caliper and a radiographic technique. Clin. Phys. Physiol. Meas. 1988, vol. 9, No. 1,57-64.

National Pork Producers Council (NPPC). 2001. Pork Quality. National Pork Procedures Council, P.O. Box 10383, Des Moines, IA.

Amin V, D. Wilson, R. Roberts, and G. Rouse, "Tissue characterization for beef grading using texture analysis of ultrasonic images," *Proc. of 1993 IEEE Ultrasonic Symposium*, pp. 969-972, 1993.

Bondestam S, A. Alanen, and S. Toikkanen, "Correlations of liver echo intensity with cytology and chemical measurements of fat, water and protein content in live burbots (*Lota lota*)," *Ultrasound in Med. and Boil*. 18, pp. 75-50,1992.

Haberkorn U, I. Zuna, A. Lorenz, H. Zerban, and G. Layer, "Echographic tissue characterization in diffuse parenchymal liver disease: Correlation of image structure with histology," *Ultrasonic Imaging* 12, pp. 155-170, 1990.

Haralick RM, K. Shanmugam and I. Dinstein, "Textural features for image classification," *IEEE Trans. Sys. Man. Cyberm*. 3, pp. 610-621, 1973.

Kim N, V. Amin, D. Wilson, G. Rouse, and S. Udpa, "Ultrasound image texture analysis for characterizing intramuscular fat content of live beef cattle," Ultrasonic Imaging, 20:191-205.

Layer G, I. Zuna, A. Lorenz, H. Zerban, and U. Haberkorn, "Computerized ultrasound B-scan texture analysis of experimental fatty liver disease: Influence of total lipid content and fast deposit distribution," *Ultrasonic Imaging* 12, pp. 171-188, 1990.

Layer G, I. Zuna, A. Lorenz, H. Zerban, and U. Haberkorn, "Computerized ultrasound B-scan texture analysis of experimental diffuse parenchymal liver disease: Correlation with histology and tissue composition," *Jn. Clin. Ultrasound* 19, pp. 193-201,1991.

Nicholas D, D. Nassiri, P. Garbutt, and C.R. Hill, "Tissue characterization from ultrasouind B-scan data," *Ultrasound in Med. and Biol*. 12, pp. 135-143, 1986.

Unser M. Texture classification and segmentation using wavelet frames. 1995. IEEE Transactions on Image Processing, 4:1549-1560.

Amin V, Wilson D, Rouse G, and Zhang H. 1995. Computerized ultrasound system for on-line evaluation of intramuscular percentage fat in *longissimus dorsi* muscle at a commercial packing facility. 1995 Beef Research Report, Iowa State University, Ames, Iowa.

Brondum, J. M. Egebo, C. Agerskov and H. Busk. 1998. On-line pork carcass grading with the Autofom ultrasound system. J. Anim. Sci. 1998. 76:1859-1868.

Faucitano, L., P. Huff, F.T. Teuscher, C. Gariepy and J. Wegner. 2005. Application of computer image analysis to measure pork marbling characteristics. Meat Sci. 69:537-543.

Hassen, A., D.E. Wilson, V. Amin, G. H. Rouse, and C.L. Hays. 2001. Predicting percentage of intramuscular fat using two types of real-time ultrasound equipment. J. Anim. Sci, 79:11-18.

Izquierdo, M.M., V.R. Amin, D.E. Wilson and G. H. Rouse. 1996. Models to predict intramuscular fat percentage in live beef animals using real-time ultrasound and image parameters: Report on data from 1991 to 1994. A.S. Leaflet R1324, Dept. Anim. Sci., Iowa State Univ., Ames, IA.

National Pork Board (NPB). 1999. Pork Quality Standards. National Pork Board, P.O. Box 9114, Des Moines, IA.

Newcom, D.W., T. J. Baas, and J.F. Lampe. 2002. Prediction of intramuscular fat percentage in live swine using real-time ultrasound. J. Anim. Sci. 80:3046-3052.

Morlein, D., R. Rosner, S. Brand, K.-V. Jenderka, and M. Wicke. 2004. Non-destructive estimation of the intramuscular fat content of the longissimus muscle of pigs by means of spectral analysis of ultrasound echoes. J. Meat. Sci. 69:187-199.

Schwab, C.R. and T.J. Baas. 2006. Development of a model to predict intramuscular fat in live pigs using real-time ultrasound. Iowa State University Animal Industry Report 2006, A.S. Leaflet 2050.

Wilson, D.E., H.L. Zhang, G.H. Rouse, D.A. Duello and M.M. Izquierdo. 1992. Prediction of intramuscular fat in the *longissimus dorsi* of live beef animals using real-time ultrasound. J. Anim. Sci. 70(Suppl. 1):224.

Silva, S.R., Afonso, J.J., Santos, V.A., Monteiro, A., Guedes, C.M., Azevedo, J.M.T., and Dias-da-Silva, A. 2006 In vivo estimation of sheep carcass composition using real-time ultrasound with two probes of 5 and 7.5 MHz and image analysis. J. Anim. Sci. 84:3433-3439.

Miller, D.C., 1998 Accuracy and Application of Real-Time Ultrasound for Evaluation of Carcass Merit in Live Animals, Department of Animal Science, NCSU.

Schinckel, A.P., Lofgren D.L., Stewart, T.S. 2000 Impact of Measurement Errors on Predicting Pork Carcass Composition: Within Sample Evaluation. Department of Animal Sciences, Purdue University.

Davis, J.K., Temple, R.S., and Mccorrmick, W.C. 1996 A Comparison of Ultrasonic Estimates of Rib-Eye Area and Fat Thickness in Cattle. J. Anim. Sci. 25:1087-1090.

Williams, A.R. 2002 Ultrasound applications in beef cattle carcass research and management. J. Anim. Sci. 80(E. Suppl. 2): E183-E-188.

Wilson, D.E. 2007 Use of Real-Time Ultrasound in % IMF Prediction for Swine. Biotronics Inc.

* cited by examiner

SYSTEMS, METHODS AND DEVICES FOR USING ULTRASONIC PROBE PRESSURE INFORMATION IN ASSESSING MUSCLE TISSUE QUALITY

RELATED DOCUMENTS

This patent document claims the benefit, under 35 U.S.C. §119(e), of U.S. Provisional Patent Application Ser. No. 61/050,539 filed on May 5, 2008, and entitled "SYSTEMS, METHODS AND DEVICES FOR USING ULTRASONIC PROBE PRESSURE INFORMATION IN ASSESSING MUSCLE TISSUE QUALITY;" this patent document and the Appendices filed in the underlying provisional application are fully incorporated herein by reference.

FEDERALLY SPONSORED RESEARCH OR DEVELOPMENT

Subject matter described in this document is based upon work supported by the Cooperative State Research, Education, and Extension Service, U.S. Department of Agriculture, under Agreement Nos. 2006-33610-16761 and 2007-33610-18441. The U.S. government has certain rights to the invention.

FIELD OF THE INVENTION

The present invention relates to systems and methods for inspecting and measuring muscle tissue parameters using ultrasound images and pressure data.

BACKGROUND

There are several attributes of muscle tissue quality that relate to palatability and consumer eating satisfaction. Assessments of such qualities can be useful for a variety of food animals. Such assessments can also be useful in both live animals and animal carcasses. For example, one such important attribute is the amount of intramuscular fat (IMF) that exists in the longissimus dorsi muscle. Within the U.S., the longissimus dorsi muscle or "loin" is a very high value part of the pork carcass. IMF in the pork loin adds significantly to flavor and juiciness, traits that are highly related to eating satisfaction. The amount of the IMF in the pork loin is governed by genetics, age of the animal at time of harvest and to a lesser degree by other environmental factors and animal nutrition.

There is considerable variation in IMF from animal to animal or from carcass to carcass with mean values in the range of 2.0-2.5%. Carcasses with less than 2.0% IMF can be undesirable. Carcasses with more than 3.5% IMF are valued by high-end restaurant chefs that offer pork on their menus. Carcasses with more than 6% IMF are highly valued in some foreign markets, such as in Japan. Because of these market differences, the ability to noninvasively measure the amount of IMF in the pork loin has value to the pork packing plant as well as to other aspects of the muscle tissue-processing industry.

A significant challenge to measuring IMF in the packing plant is the speed by which carcasses are processed. As an example, with many plants running their chain speed at 1200 carcasses per hour, a carcass would be measured in less than 2 seconds if the carcass is going to be measured during the packing process. In addition, pork carcasses are not routinely split anywhere along the loin that would expose the internal tissue for either a subjective or quantitative measure of the amount of IMF in the lean tissue. Consequently, packing plants have sought efficient and practical methods of noninvasively "looking" inside the loin muscle and determining the percentage of IMF as compared to the amount of lean tissue.

SUMMARY

The present invention is directed to systems and methods for inspecting aspects, such as content and quality of muscle tissue using ultrasound, and for properly and consistently applying ultrasound transducer probes in a manner that promotes acquisition of useable data. These and other aspects of the present invention are exemplified in a number of illustrated implementations and applications, some of which are shown in the figures and characterized in the claims section that follows.

Consistent with an embodiment of the present invention, a method is implemented for measuring muscle tissue characteristics such as the relative content of intramuscular fat (IMF) in a portion of muscle tissue. An ultrasound probe is presented to the portion of carcass skin covering subcutaneous fat and muscle tissue. The probe produces a response-provoking signal in the muscle tissue, and the pressure applied between the probe and the portion of carcass skin is sensed. A resulting signal is used to determine the muscle tissue characteristics as a function of the pressure being exerted between the probe and the portion.

In a specific embodiment, the pressure signals are used to filter the acquisition or use of ultrasound image data, for example, preventing capture or use of image data associated with pressure readings that fall outside of an acceptable pressure range.

In other specific embodiments, captured image data is analyzed by weighing or otherwise adjusting the measured muscle tissue characteristic according to the resulting signal by accounting for the associated pressure readings.

The above overview is not intended to describe each illustrated embodiment or every implementation of the present invention. The figures and detailed description that follow and in the appended claims, more particularly exemplify these embodiments.

BRIEF DESCRIPTION OF THE DRAWINGS

The invention may be more completely understood in consideration of the detailed description of various embodiments of the invention that follows in connection with the accompanying drawings in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for inspecting and measuring muscle tissue parameters, such as fat and lean composition and quality of muscle tissue. The muscle tissue can originate from any number of different food animals and the inspection and measuring can be obtained from live animals or animal carcasses. A specific embodiment of the present invention facilitates measurement of intramuscular fat (IMF) of a pork carcass. Unless otherwise stated, the term "animal" refers to either a live animal or an animal carcass. While the present invention is not necessarily limited to such applications, various aspects of the invention may be appreciated through a discussion of various examples using this context.

An embodiment of the present invention is directed toward a noninvasive mechanism for determining IMF content of muscle tissue, such as muscle tissue from live swine or pork carcasses. Ultrasound imaging is used to capture internal images of the muscle tissue. Specific embodiments of the present invention are directed toward facilitating the determination of pork loin IMF content in a pork-carcass processing line (e.g., in a muscle tissue packing plant). Devices, methods and systems facilitate IMF content determinations at speeds and accuracy levels that are particularly useful for use on a processing line.

Embodiments of the present invention facilitate proper placement of an ultrasound transducer on the skin of the carcass. The inventors have recognized and appreciated that accurate muscle tissue characterization can be obtained by ensuring that images used in determining the muscle tissue characteristics are acquired using the proper pressure between the ultrasound transducer and the carcass skin. In a specific embodiment, one or more pressure sensors are used to provide feedback regarding the pressure between the ultrasound transducer and the pork carcass skin. The measurements may be made real-time on carcasses that are moving on a transport rail at a nearly constant rate of 1,200 carcasses per hour. Measurements are made from live video-streaming ultrasound images as the carcasses move past a scanning station. The scanning station can be fully automated, manual or a combination thereof.

Figure 1A:
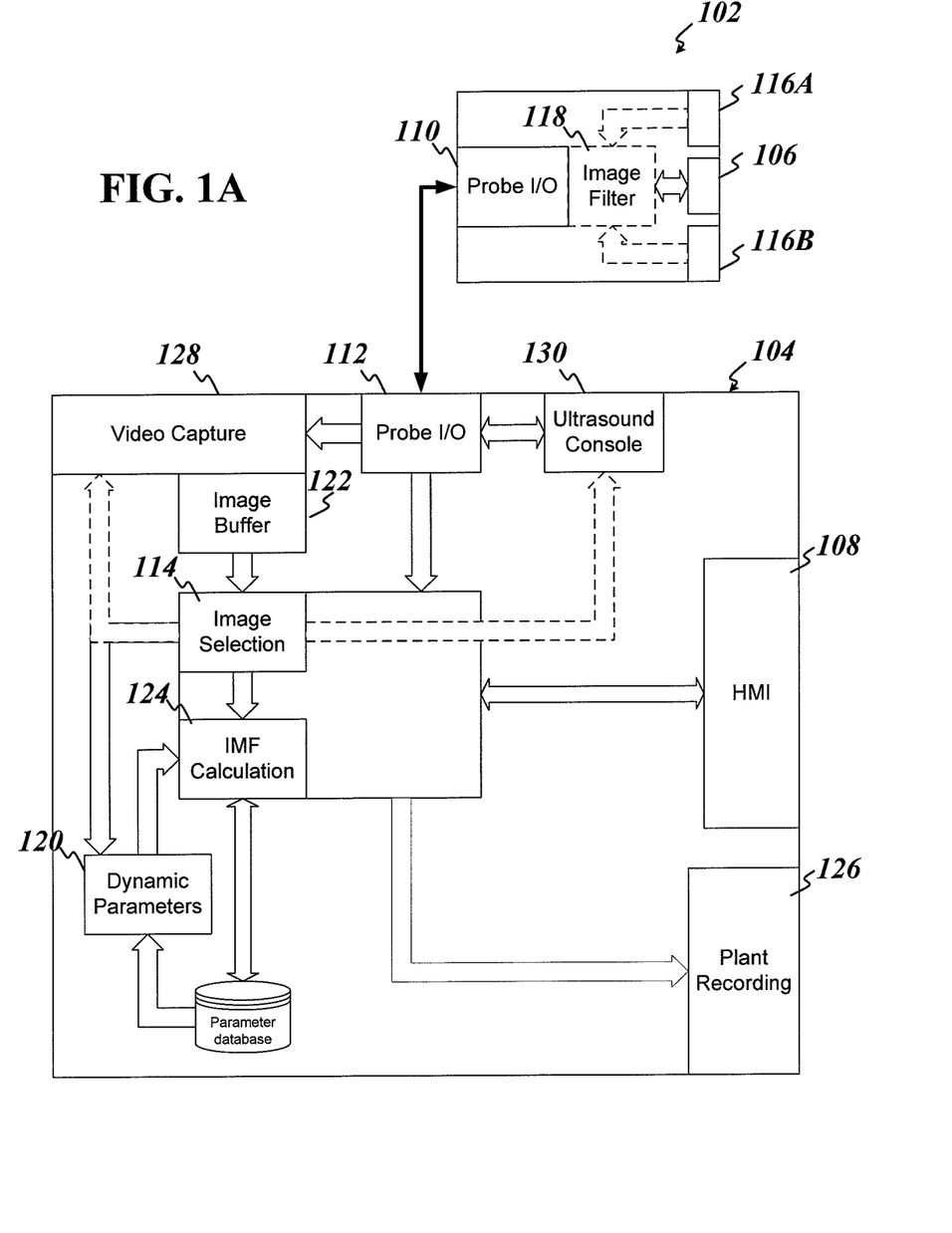
FIG. 1A shows a system-level diagram, consistent with an example embodiment of the present invention.
Figure 1B:
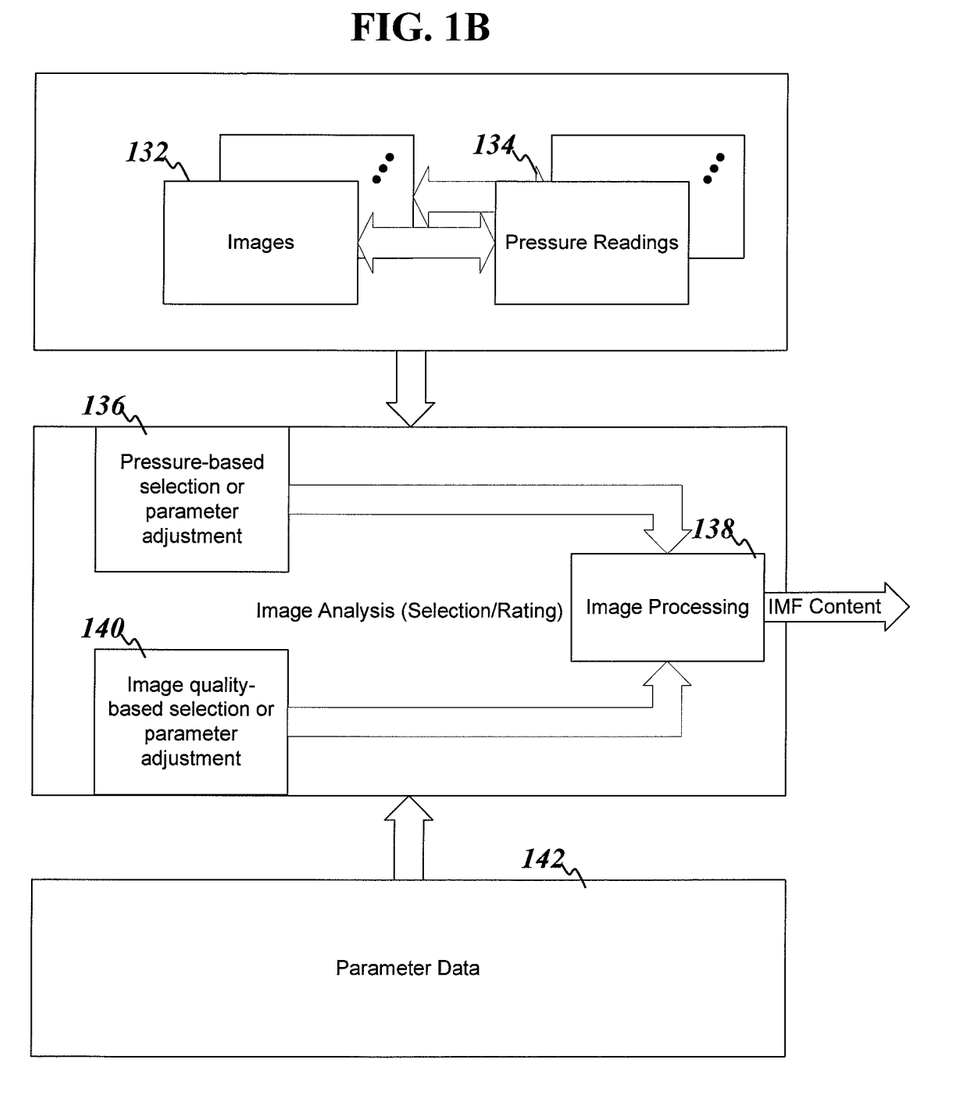
FIG. 1B shows a flow diagram for determining muscle tissue characteristics, consistent with an example embodiment of the present invention.

By way of example, FIGS. 1A and 1B illustrate a system for use in inspecting and measuring muscle tissue parameters in carcasses, according to an embodiment of the present invention. Probe 102 communicatively connects to processing block 104 using probe input/output (I/O) 110, 112. This connection can be implemented using, for example, a wired connection, wireless connections or a removable storage medium. Wired connections can be implemented using any suitable (e.g., bandwidth and reliability) protocol including, but not limited to, universal serial bus (USB), IEEE 1394 and Ethernet. In a specific instance, the probe is connected using a data-carrying cable (e.g., electrical or optical). In another instance, the probe is integrated into a single device that includes the processing block 104. Wired connections can also be implemented using a more temporary connection, such as a removable data storage device or a cradle for placement of the probe. Wireless connections for non-ultrasound communications can be implemented using an assortment of different techniques and protocols including, but not limited to, 802.11x or ultra-wideband (UMB).

Probe 102 provides images of the carcass using ultrasound imaging. An ultrasound transducer 106 converts control data into transmitted sound and received sound into image data. In a specific example, the transducer is a piezoelectric transducer that converts between electrical and physical vibration energy. Embodiments of the invention are designed to allow use of a variety of existing or future imaging techniques (e.g., other than piezoelectric transducers). The actuation of such transducers can be controlled by ultrasound controller 130. For example, controller 130 can provide a stimulus profile for capturing a series of images from the same carcass.

Embodiments of the invention include a human-machine interface (HMI) 108. HMI 108 facilitates operation, monitoring or otherwise interfacing with the system by a human operator.

Image selection block 114 is an optional component that selects between a set of images obtained from the probe 102. Image selection block may facilitate the selection of images based on direct or secondary indicia of image quality or usability. For example, acquired images may be screened for blurriness, the existence or absence of certain features, the existence or absence of one or more subset regions of interest (ROI) within the image, and for conditions under which the images were acquired.

With respect to image acquisition conditions, it has been observed that the quality and repeatability of ultrasonic images acquired from animal carcasses can be affected by the pressure applied between the probe transducer and the carcass skin. Thus, in reference to FIG. 1A, the probe 102 optionally includes one or more pressure sensors such as load cells 116A and 116B. Information from the pressure sensors may be used by an image filter 118 within the probe 102 to decide whether to capture and transmit images to the processing block 104. In other embodiments, the pressure data is transmitted to the processing block 104 for analysis, at which point the images may be recorded using video capture 128 and/or buffer 122 and retained for further analysis or discarded based on the pressure readings. In another example, the processing block 104 analyzes the pressure data and in response determines whether or not to activate the ultrasound transducer. Feedback signals may be provided to control further image acquisition by the probe and/or to provide an operation status indication (e.g., yellow light for non-acquisition stand-by mode when the probe is not applied or insufficient pressure is applied, red light for non-acquisition based on too much pressure or unbalanced pressure, and green light for ultrasonic activation and image acquisition due to proper application of the probe).

During image selection screening, images are removed or discarded if the quality and/or pressure criteria are not met. In certain embodiments, images discarded based on such screening may be stored for later analysis, for example, to facilitate system diagnostics, for adjusting of screening algorithm parameters, and so forth.

According to specific embodiments of the present invention, the processing parameters 120 used by the algorithms for determining IMF percentage estimates can be dynamically adjusted for each carcass. For example, each carcass has a specific makeup with regards to the tissue depths of various tissue types. These differences can affect the captured image data as, for example, different tissue types can exhibit different sound propagation properties. Tissue types that can be monitored for dynamic adjustments include, but are not limited to, subcutaneous fat, muscle (loin), skin and bones. In a specific instance, the subcutaneous fat depth and loin depth within a region of interest are determined. These determined depths are then used as parameters in the algorithms for the specific carcass.

The IMF percentage estimation 124 can be provided for immediate viewing using HMI 108 and/or recorded 126 for future use (e.g., sorting, recording, pricing and feedback for genetic profiling).

FIG. 1B shows a flow diagram for providing an IMF content estimation, according to an example embodiment of the present invention. The system stores a set of images obtained from a carcass 132. These images can be associated with pressure readings 134. The association can be an explicit data bit stored with the images (e.g., database association or tag added to the images) or can be implicit due to filtering of the images prior to storage (e.g., the act of storing implies that the images fall within the desired pressure range). Image processing 138 involves use of the set of images 132 to calculate the IMF percentages. One component of image processing 138 involves parameter data 142. Other components can include, for example, pressure-based selection or parameter adjustment 136 and/or image quality-based selection or parameter adjustment 140. Each of these components 136 and 140 can be used to exclude various images, such as those that do not meet pressure or image quality criterion. Alternatively, (or in addition to such image exclusion), components 136 and 140 can be used to modify the parameters 142 for respective images. In one instance, this modification can take the form of reduction in the statistical contribution of images with less-than-ideal pressure readings or having low-quality of image (e.g., blurred images or images with poor contact). In another instance, the modification can include compensations to the parameter data 142. For example, images associated with certain low pressure readings may result in incorrect IMF content estimates. Where such incorrect IMF content estimates deviate from the actual IMF content by a predictable amount, the estimates can be adjusted accordingly.

Figure 2:
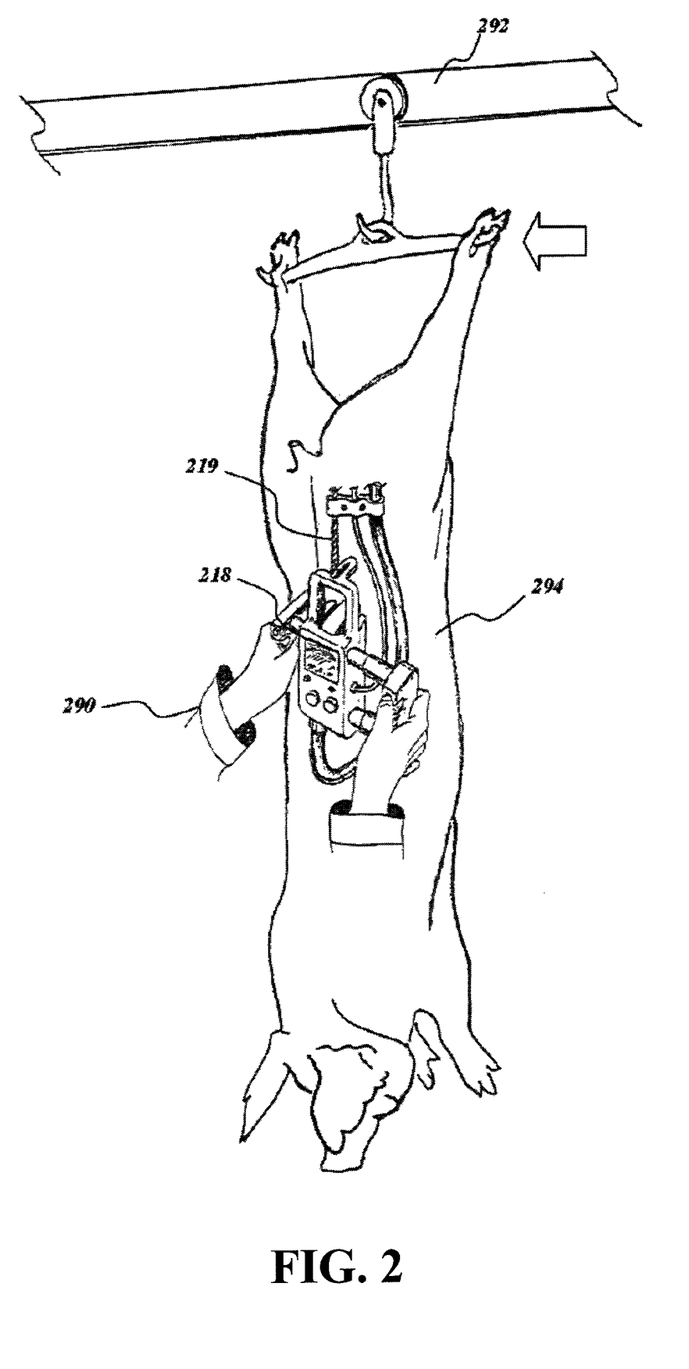
FIG. 2 illustrates ultrasonic scanning of a hot carcass within a packing plant environment, consistent with an example embodiment of the present invention.

By way of example, FIG. 2 illustrates a packing plant environment where hot carcasses, such as carcass 294, are conveyed along an overhead conveyor system 292 in a direction indicated by the arrow. As the carcasses pass an operator measurement position, an operator 290 applies an ultrasonic transducer probe from ultrasound system 218 to a specified portion of the carcass 294. Images acquired from the ultrasound system 218 are provided via connection 219 to a data acquisition system for data analysis.

Systems in accordance with certain embodiments include a hardware subsystem that includes I/O components for obtaining data from a carcass and for interfacing with an operator. A data processing subsystem includes components for screening and processing data and for providing results for output. While a number of different implementation options exist (e.g., the data processing subsystem may be suitably implemented using hardware circuitry, programmable logic devices, firmware, software, and combinations thereof).

In one embodiment, the ultrasonic probe includes one or more pressure sensors located close to the transducer face, for example, one pressure sensor near the top of the transducer face and one pressure sensor near the bottom or an array of pressure sensors dispersed about the transducer face. The pressure sensor(s) are responsive to the transducer face contacting the carcass and provide a signal to the system that is used to record the pressure applied between the transducer face and the carcass. The recorded pressure data is associated with the images taken while at the respective pressure signal, and may be used for image screening (e.g., only images associated with pressure readings greater than a threshold value or falling within a specified range are analyzed) and/or for correction of output value (e.g., pressure data may be correlated to correction values that can be applied to the system results prior to outputting a final value). Pressure data may also be used to facilitate proper application of the transducer fixture to the carcass. For example, LEDs may be incorporated into the transducer fixture to implement a three-color light scheme whereby yellow indicates a standby status where the transducer is not on the carcass, green indicates that the transducer is on the carcass and the applied pressure is at a predetermined level or within a predetermined range (e.g., controlled or specified in software), and red indicates a fault situation such as when the applied pressure is too high for proper data acquisition, an insufficient number of valid data frames were acquired during a data acquisition time frame, and so forth.

The load cells of a transducer fixture sense the force applied between the ultrasound probe and the carcass skin. The load cells convert the force acting on it into a measurable electrical signal. Changes in the load result in a proportional change in the signal. Any suitable load cell may be used including, but not limited to, displacement sensors that sense variable capacitance between electrodes with respect to movement of the electrodes in response to an applied force. In-line amplifiers may be used to boost the strength of the load cell signals to a level usable by the data acquisition system. The amplifiers may be adjustable for each load cell, for example, to respond by outputting 0.5 Volts for every 1 pound of force applied. Force data is sent through the data acquisition system to the capturing software and recorded with the images. Software may be used to decide if the ultrasonic probe transducer face is properly positioned and to provide feedback status information, for example, visually through probe force status LEDs.

Measurement of carcasses online in packing plants can be performed by human operators with the aid of measuring devices. However, humans tire and become distracted when doing monotonous activities. A robotic system offers repeatability and precision in application of the measuring device, even on moving carcasses. For example, a robotic system may employ a six-degrees-of-freedom arm guided by laser-vision sensors that scan each carcass to determine the precise positioning of the transducer and its fixture on the carcass. Variation in size and shape of individual carcasses can be accounted for so that linear measurement of subcutaneous fat and muscle measurements are made at the same relative anatomical position on every carcass. Various alternative location techniques can also be employed. For example, a human could mark a target location on the carcass (e.g., placing a visible mark on the carcass at the appropriate location). The automated arm can search for the marked location and properly place the ultrasound sensor based upon the marked location. This can be particularly useful for reducing the complexity of the positioning determination (e.g., simplifying automated machine vision and image processing) while allowing the actual placement and contacting of the ultrasound sensor to remain automated. Proximity and pressure sensors are used to insure that the transducer face is properly applied to the carcass for the capturing of images required for loin muscle tissue characterization for the prediction of percentage intramuscular fat.

A specific embodiment of the present invention includes a pressure sensing fixture that mounts to the ultrasonic transducer and that can be disassembled for cleaning or repair as needed. In certain embodiments, the pressure sensing fixtures include two pressure load cells located and operated perpendicular to the face of the ultrasonic transducer (i.e., parallel to the direction of ultrasound wave propagation). In an exemplary arrangement, one load cell is located near the top end of the transducer (e.g., within 1 cm of the top) or near one end of the transducer and the second load cell is located near the bottom end of the transducer (e.g., within 1 cm of the bottom) or near the opposite end of the transducer. In another exemplary arrangement, the load cells are embedded into and are a part of the transducer lens and are an integral part of the transducer probe. These load cells indirectly measure the pressure being applied between the transducer lens face and the carcass as the transducer is applied to the carcass skin surface by the human operator or by a robotic arm.

Software algorithms or hardware are used to monitor the pressure readings from each load cell. The system associates the pressure readings with the video frames that were captured at the same time that the readings were acquired. In certain embodiments, live video streaming frames are used to calculate IMF content only when the load cell readings indicate that the transducer is being applied to the skin of the carcass within a specified range of pressure, for example, pressure higher than a minimum threshold, pressure lower than a maximum threshold, and/or pressure difference between the load cells is less than a maximum difference. The software may be used to control indicators such as two LEDs, one for each load cell. The processing software sends a code for turning the LED yellow if the pressure for that particular load cell has not reached a minimum level for acquiring images that allow proper tissue texture analysis. The processing software sends a code for turning the LED green when an appropriate pressure or pressure range is achieved. The processing software sends a code for turning the LED red if the pressure exceeds an acceptable pressure level. The frames captured outside the allowable pressure range may be rejected as not suitable for processing, although they may be saved for later analysis and system diagnostics purposes. Pressure level parameters within the processing software may be adjustable by service technicians and allow for maintaining proper calibration of the fixture and sensor configuration.

Figure 3A:
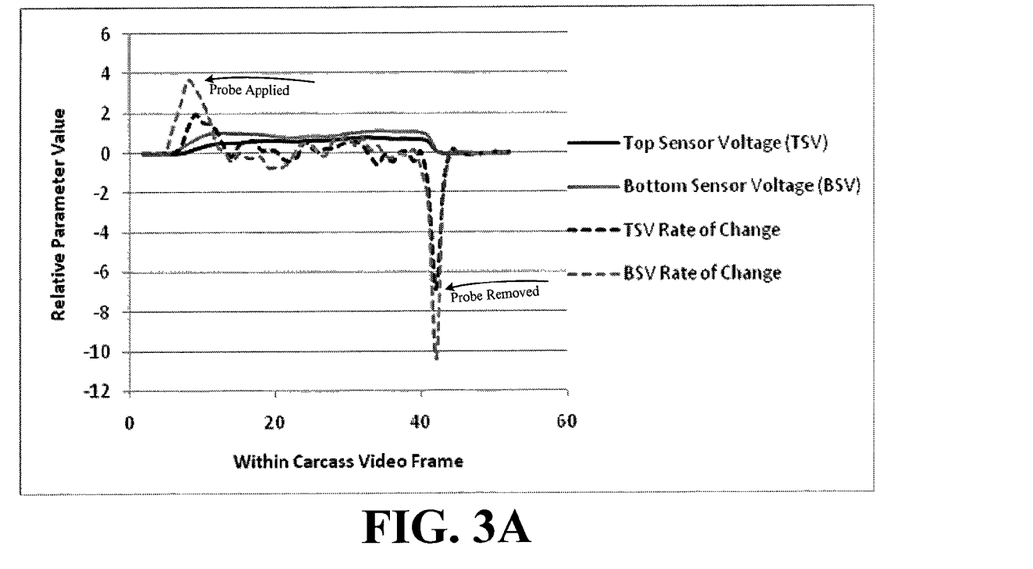
FIG. 3A illustrates the change in the voltage and voltage change rate for top and bottom pressure sensors within a carcass video frame, consistent with an example embodiment of the present invention.
Figure 3B:
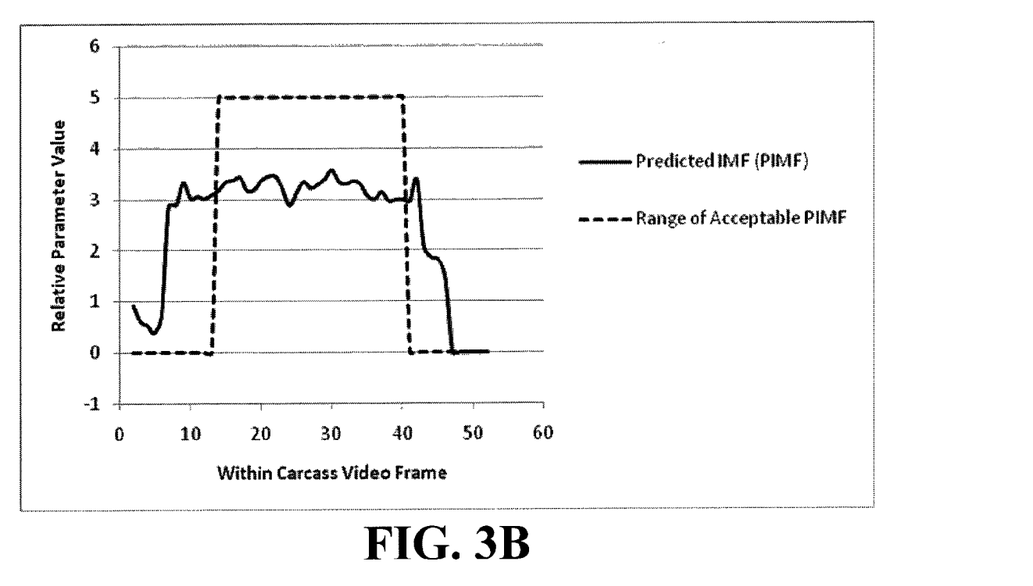
FIG. 3B illustrates the predicted IMF and the range of acceptable predicted IMF within a carcass video frame, consistent with an example embodiment of the present invention.
Figure 3C:
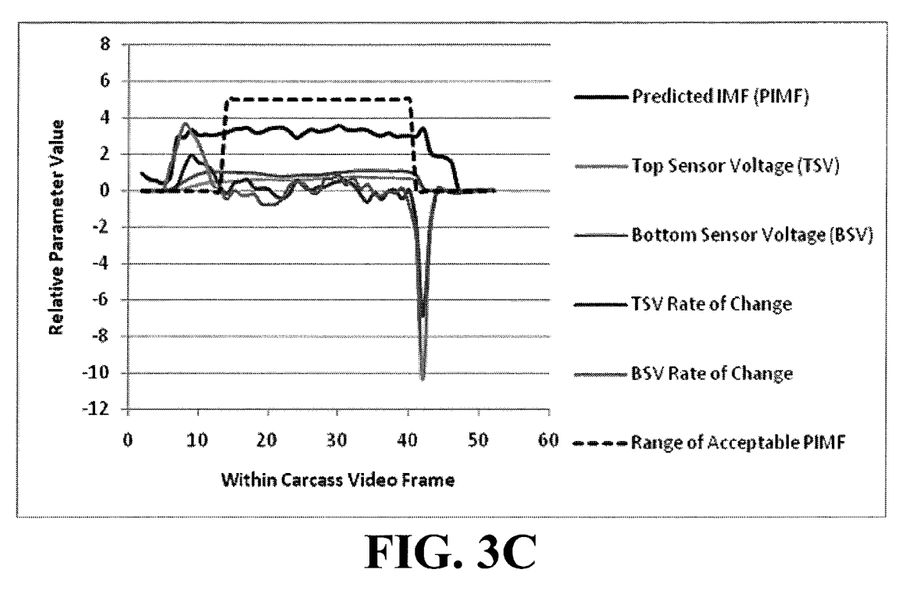
FIG. 3C illustrates the dependence of predicted IMF on the rate of change of voltages for top and bottom pressure sensors, consistent with an example embodiment of the present invention.

FIGS. 3A, 3B and 3C illustrate the dependence of predicted IMF on the pressure exerted by the transducer on the skin of the carcass. In FIG. 3A, the plot shows the voltage level being sent from the top pressure sensor and the bottom pressure sensor. The voltage level increases as pressure increases, e.g., as the transducer is being applied to the skin surface. The voltage level for each sensor increases to some steady state value as the operator seeks to stabilize the quality of the video stream of frames, with only minor change in value being seen. FIG. 3A also shows the rate of change of each sensor's voltage level. When the transducer is being applied to the skin of the carcass, and then again when the transducer is being removed, the voltage rates of change are at their peak values. An unexpected result is that both the voltage level and the rate of change of voltage are important parameters for the pressure filter. To provide high-levels of the accuracy in the tissue characterization, it can be important to verify that the image frames were captured with both the correct threshold range of pressure and a stabilized rate of change that is also within a maximum threshold range. For example, if the current or previous frame sensor voltage is less than or equal to 0.49, then the current frame is ignored. Concurrently, if the difference between the current frame voltage and the previous frame voltage divided by 0.067 (the voltage rate change) is greater than 1.3, the current frame is ignored.

FIG. 3B shows the surprisingly accurate predicted IMF as it relates to the series of image frames corresponding to the pressure sensor values of FIG. 3A. As shown, the acceptable period for predicting IMF is surprisingly correlated with the parameters from the pressure sensor. FIG. 3C shows the overlay of the data from FIGS. 3A and 3B, further showing the surprising correlation between the pressure sensor input and the predictive accuracy in IMF measurement.

Figure 4:
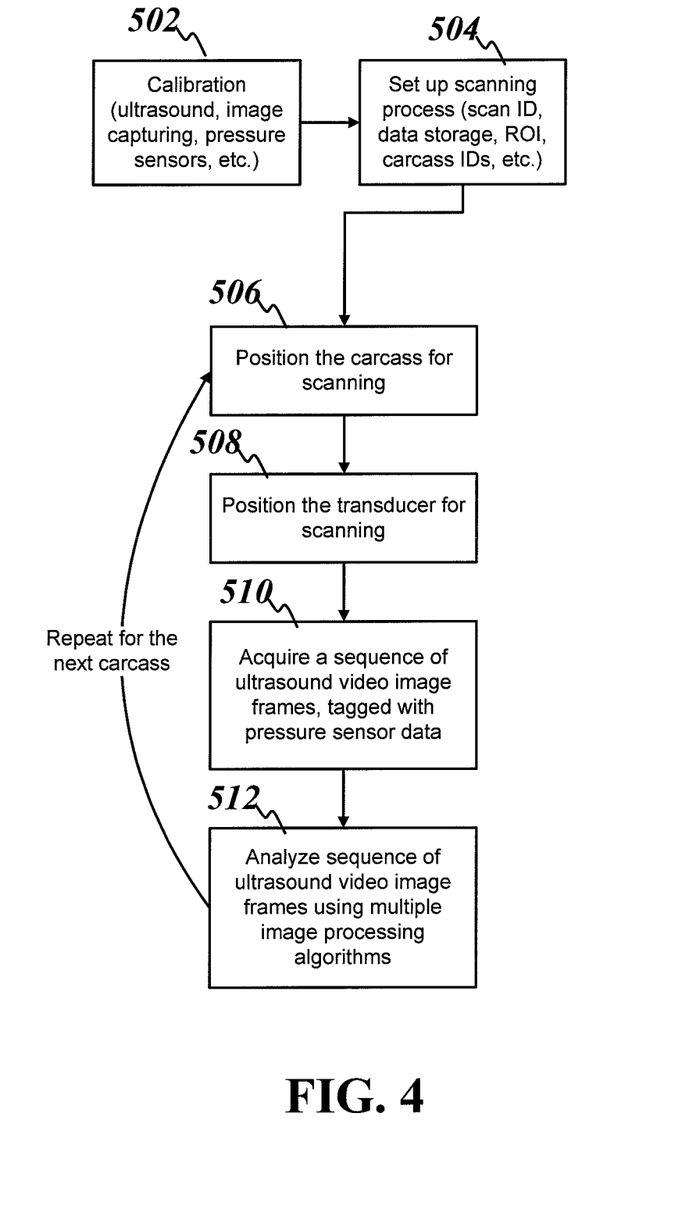
FIG. 4 presents an overall flow chart of an image acquisition procedure, consistent with an example embodiment of the present invention.

FIG. 4 presents an overall flow chart of an image acquisition procedure in accordance with certain embodiments. At step 502 the device can optionally be calibrated. Calibration can include testing and configuration of a number of different elements including, but not limited to, ultrasound, image capturing and pressure sensors. At step 504 the scanning process is setup. This can include scanning of carcass IDs, data storage of necessary information, ROI determinations and the like. At step 506 the carcass is positioned for scanning. The transducer is positioned (e.g., placed in contact with the carcass skin) for scanning at step 508. Step 510 involves the acquisition of a sequence of ultrasound video image frames. These images can be tagged with pressure sensor data, or otherwise filtered according to the pressure data. At step 512, the sequence of ultrasound video image frames are analyzed using multiple image processing algorithms. Steps 506-512 can then be repeated for subsequent carcasses as desired.

The amount of time varies that a probe is positioned on a carcass to capture live ultrasound video. Also, the number of acceptable frames varies from carcass to carcass. It has been observed that the IMF prediction model is most accurate using images captured when the probe is effectively positioned on the carcass (defined by acceptable images being captured) for about 1 or more seconds.

The number and diversity of the various embodiments show the surprising versatility and effectiveness of the devices and methods associated with embodiments of the present invention. For instance, the surprising effectiveness and accuracy of the developed image processing algorithms facilitates usage in a variety of applications and environments. In another instance, the flexibility to apply filters to the data and algorithms provides a surprisingly robust and efficient solution to a number of different problems. Thus, the embodiments disclosed herein should not be viewed as limiting and should be recognized as providing support for a variety of variations and related applications.

One such application relates to a method of assessing tissue characteristics or attributes in a portion of muscle tissue. The method includes selecting a region of interest within an image of the portion of muscle tissue; applying image texture processing to the region of interest; and extracting, responsive to the image texture processing, tissue characteristics or attributes of the portion of muscle tissue. The step of selecting a region of interest within an image of the portion of muscle tissue can include the use of fat and loin depth measurements and/or rib boundaries. In some instances, a set of texture parameters derived from images of the portion of muscle tissue can be used in combination with a prediction formula.

Other applications relate to one or more of the following. Regression modeling, statistical editing or pass filter can be used in accordance with any embodiments of the present invention. Images can be filtered based upon one or more of pressure sensing, histogram thresholding, grey-scale gating, reflection intensities, blurriness, contrast levels, undesirable echo artifacts, and electromagnetic interference. Systems, algorithms or parameters can be normalized across a variety of devices and components. Automated positioning systems can be used for placement of an image probe/sensor on a portion of muscle tissue in accordance with a variety of embodiments. Different portions of muscle tissue can be sorted as a function of determined characteristics for portions of muscle tissue. The devices, methods, systems or arrangements of various embodiments of the invention can be applied to live animals, which can be useful for determining animal yield and quality calculations for the animals.

Aspects of the present invention lend themselves to implementations in a variety of devices including, but not limited to, hardware circuitry, programmable logic devices, firmware, software, and combinations thereof. A specific example includes computer readable medium storing computer executable instructions that when executed by a processor perform one or more of the process steps. The implementations of the various algorithms and methods described herein effectively transform what would otherwise be a general purpose processor into a specially-programmed processor that is configured and arranged to implement the specialized algorithms.

It should be apparent that the various methods and algorithms discussed herein represent more than abstract concepts and mental steps. For instance, embodiments of the present invention relate to the transformation of specific image-based content and include hardware interfaces with various input and output devices.

While the present invention has been described in the above description and in the claims that follow, those skilled in the art will recognize that changes may be made thereto without departing from the spirit and scope of the present invention. Such changes may include, for example, the implementation of one or more approaches that are variations of those approaches expressly disclosed herein. These and other approaches as described in the contemplated claims below characterize aspects of the present invention.

What is claimed is:

1. A circuit-implemented method of measuring muscle tissue characteristics in a portion of muscle tissue of a food animal, the method comprising:
   to the portion of muscle tissue, presenting an ultrasound probe for producing an ultrasound signal;
   generating a pressure signal as a function of sensed pressure applied between the probe and the food animal, by generating an electrical signal for a top pressure sensor and an electrical signal for a bottom pressure sensor;
   acquiring ultrasound image data responsive to the ultrasound signal and dependent on the pressure signal;
   comparing the generated pressure signal with an acceptable pressure range;
   filtering the image frames, corresponding to the ultrasound image data, for which the generated pressure signal is not within the acceptable pressure range;
   computing, between a pair of consecutive image frames, a top electrical change rate for the top pressure sensor as a function of a difference between the electrical signal for the top pressure sensor for consecutive image frames and a frame capturing rate;
   computing, between a pair of consecutive image frames, a bottom electrical change rate for the bottom pressure sensor as a function of a difference between the electrical signal for the bottom pressure sensor for the consecutive image frames and the frame capturing rate;
   filtering the image frames for which either of the computed electrical signal change rates exceeds a predefined maximum threshold; and
   using the filtered image frames to measure muscle tissue characteristics.

2. A circuit-implemented method of measuring muscle tissue characteristics in a portion of muscle tissue of a food animal, the method comprising:
   to the portion of muscle tissue, presenting an ultrasound probe for producing an ultrasound signal;
   generating a pressure signal as a function of sensed pressure applied between the probe and the food animal;
   acquiring ultrasound image data responsive to the ultrasound signal and dependent on the pressure signal; and
   using the acquired image data to measure muscle tissue characteristics;
   wherein generating a pressure signal includes generating electrical signals for first and second pressure sensors,
   further including filtering image frames corresponding to the ultrasound image data based upon a rate of change of at least one of the respective electrical signals, and
   wherein using the acquired image data to measure muscle tissue characteristics includes using the filtered image frames to measure the muscle tissue characteristics.

* * * * *